(12) United States Patent
Grey et al.

(10) Patent No.: US 8,124,798 B2
(45) Date of Patent: Feb. 28, 2012

(54) DIRECT EPOXIDATION CATALYST AND PROCESS

(75) Inventors: Roger A. Grey, West Chester, PA (US); Robert N. Cochran, West Chester, PA (US); Bi Le-Khac, West Chester, PA (US)

(73) Assignee: Lyondell Chemical Technology, LP, Houston, TX (US)

( * ) Notice: Subject to any disclaimer, the term of this patent is extended or adjusted under 35 U.S.C. 154(b) by 0 days.

(21) Appl. No.: 12/653,678

(22) Filed: Dec. 17, 2009

(65) Prior Publication Data

US 2011/0152550 A1    Jun. 23, 2011

(51) Int. Cl.
  *C07D 301/12* (2006.01)
  *C07D 301/06* (2006.01)
  *B01J 29/06* (2006.01)

(52) U.S. Cl. ......... 549/531; 549/532; 549/533; 502/66

(58) Field of Classification Search ............... 549/531, 549/532, 533; 502/66
See application file for complete search history.

(56) References Cited

U.S. PATENT DOCUMENTS

| | | | |
|---|---|---|---|
| 3,351,635 A | 11/1967 | Kollar | |
| 4,367,342 A | 1/1983 | Wulff et al. | |
| 4,410,501 A | 10/1983 | Taramasso et al. | |
| 4,666,692 A | 5/1987 | Taramasso et al. | |
| 4,833,260 A | 5/1989 | Neri et al. | |
| 4,859,785 A | 8/1989 | Bellussi et al. | |
| 4,937,216 A | 6/1990 | Clerici et al. | |
| 5,989,648 A | 11/1999 | Phillips | |
| 6,008,388 A | 12/1999 | Dessau et al. | |
| 6,399,794 B1 | 6/2002 | Hancu | |
| 6,495,259 B1 | 12/2002 | Kasner | |
| 6,534,661 B1 | 3/2003 | Zhou et al. | |
| 6,958,255 B2 | 10/2005 | Khuri-Yakub et al. | |
| 7,030,255 B2 | 4/2006 | Grey et al. | |
| 7,399,726 B2 | 7/2008 | Cooker et al. | |
| 7,453,003 B1 | 11/2008 | Le-Khac | |
| 7,501,532 B1 | 3/2009 | Le-Khac | |
| 7,531,675 B1 | 5/2009 | Grey | |
| 2008/0021230 A1 | 1/2008 | Qin et al. | |

FOREIGN PATENT DOCUMENTS

| | | |
|---|---|---|
| GB | 1001038 | 6/1989 |
| JP | 4-352771 | 12/1992 |
| WO | 2009/054376 A1 | 4/2009 |

OTHER PUBLICATIONS

Artemov, A. V., New highly efficient catalysts for liquid-phase oxidation, 2001, Kataliz v Promyshlennosti, (2), 18-23, (abstract page).*
Wu et al., "A Novel Titanosilicate with MWW Structure. I. Hydrothermal Synthesis, Elimination of Extraframework Titanium, and Characterizations," Journal Of Physical Chemistry B, 105, (2001), p. 2897-2905.
J. Edler & J. White, "Room-temperature Formation of Molecular Sieve MCM-41," J. Chem. Soc. Chem. Comm., (1995), 155.
D. Renzo, "A 28-year-old synthesis of micelle-templated mesoporous silica," *Microporous Materials*, 10 (1997), 283-286.

* cited by examiner

*Primary Examiner* — Taylor Victor Oh

(57) ABSTRACT

A catalyst, useful for the direct epoxidation of olefins, is disclosed. The catalyst comprises palladium nanoparticles, support nanoparticles, and a titanium zeolite having a particle size of 2 microns or greater. The palladium nanoparticles are deposited on the support nanoparticles to form supported palladium nanoparticles, and the supported palladium nanoparticles are deposited on the titanium zeolite; or the supported palladium nanoparticles are deposited on a carrier having a particle size of 2 microns or greater. The invention also includes a process for producing an epoxide comprising reacting an olefin, hydrogen and oxygen in the presence of the catalyst. The catalysts are more active in epoxidation reactions, while demonstrating the same or better selectivity.

19 Claims, No Drawings

DIRECT EPOXIDATION CATALYST AND PROCESS

FIELD OF THE INVENTION

This invention relates to a catalyst and its use in the production of epoxides.

BACKGROUND OF THE INVENTION

Many different methods for the preparation of epoxides have been developed. Generally, epoxides are formed by the reaction of an olefin with an oxidizing agent in the presence of a catalyst. Ethylene oxide is commercially produced by the reaction of ethylene with oxygen over a silver catalyst. Propylene oxide is commercially produced by reacting propylene with an organic hydroperoxide oxidizing agent, such as ethylbenzene hydroperoxide or tert-butyl hydroperoxide. This process is performed in the presence of a solubilized molybdenum catalyst, see U.S. Pat. No. 3,351,635, or a heterogeneous titania on silica catalyst, see U.S. Pat. No. 4,367,342.

Besides oxygen and alkyl hydroperoxides, hydrogen peroxide is also a useful oxidizing agent for epoxide formation. U.S. Pat. Nos. 4,833,260, 4,859,785, and 4,937,216, for example, disclose olefin epoxidation with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation process. Typically, the catalyst comprises a noble metal and a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form a hydrogen peroxide in situ oxidizing agent. U.S. Pat. No. 6,498,259 describes a catalyst mixture of a titanium zeolite and a supported palladium complex, where palladium is supported on carbon, silica, silica-alumina, titania, zirconia, and niobia. Other direct epoxidation catalyst examples include gold supported on titanosilicates, see for example PCT Intl. Appl. WO 98/00413.

One disadvantage of the described direct epoxidation catalysts is that they are prone to produce non-selective byproducts such as glycols or glycol ethers formed by the ring-opening of the epoxide product or alkane byproduct formed by the hydrogenation of olefin. U.S. Pat. No. 6,008,388 teaches that the selectivity for the direct olefin epoxidation process is enhanced by the addition of a nitrogen compound such as ammonium hydroxide to the reaction mixture. U.S. Pat. No. 6,399,794 teaches the use of ammonium bicarbonate modifiers to decrease the production of ring-opened byproducts.

U.S. Pat. No. 6,005,123 teaches the use of phosphorus, sulfur, selenium or arsenic modifiers such as triphenylphosphine or benzothiophene to decrease the production of propane. U.S. Pat. No. 7,026,492 discloses that the presence of carbon monoxide, methylacetylene, and/or propadiene modifier gives significantly reduced alkane byproduct. U.S. Appl. Pub. No. 2008/0021230 discloses that the use of a lead-modified palladium-containing titanium or vanadium zeolite reduces alkane byproduct formation. In addition, co-pending U.S. Pat. Appl. Ser. No. 11/977,360 teaches that the use of a catalyst comprising titanium or vanadium zeolite, a noble metal, lead, and bismuth also reduces alkane byproduct formation.

As with any chemical process, it is desirable to attain still further improvements in the epoxidation methods and catalysts. We have discovered a new catalyst and its use in olefin epoxidation.

SUMMARY OF THE INVENTION

The invention is a catalyst comprising palladium nanoparticles, support nanoparticles, and a titanium zeolite having a particle size of 2 microns or greater. The palladium nanoparticles are deposited on the support nanoparticles to form supported palladium nanoparticles. The supported palladium nanoparticles are deposited on the titanium zeolite; or the supported palladium nanoparticles are deposited on a carrier having a particle size of 2 microns or greater. The catalyst is useful in olefin epoxidation. Thus, the invention also includes an olefin epoxidation process that comprises reacting olefin, oxygen, and hydrogen in the presence of the catalyst. This catalyst is more active than comparable catalysts while demonstrating similar or better olefin selectivity.

DETAILED DESCRIPTION OF THE INVENTION

The catalyst of the invention comprises palladium nanoparticles, support nanoparticles, and a titanium zeolite having a particle size of 2 microns or greater. Titanium zeolites comprise the class of zeolitic substances wherein titanium atoms are substituted for a portion of the silicon atoms in the lattice framework of a molecular sieve. Such substances, and their production, are well known in the art. See for example, U.S. Pat. Nos. 4,410,501 and 4,666,692.

Suitable titanium zeolites are those crystalline materials having a porous molecular sieve structure with titanium atoms substituted in the framework. The choice of titanium zeolite employed will depend upon a number of factors, including the size and shape of the olefin to be epoxidized. Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the is ZSM-11 aluminosilicate zeolites), "TS-3" (as described in Belgian Pat. No. 1,001,038), and Ti-MWW (having a topology analogous to that of the MWW aluminosilicate zeolites). Titanium-containing molecular sieves having framework structures isomorphous to zeolite beta, mordenite, ZSM-48, ZSM-12, SBA-15, TUD, HMS, and MCM-41 are also suitable for use. TS-1 and Ti-MWW are particularly preferred. The titanium zeolites preferably contain no elements other than titanium, silicon, and oxygen in the lattice framework, although minor amounts of boron, iron, aluminum, sodium, potassium, copper and the like may be present.

The titanium zeolites having a size of 2 microns or greater may be a large particle size titanium zeolite produced, for example, according to the procedure described in U.S. Pat. No. 7,399,726. Preferably, the titanium zeolite is produced by spray drying, pelletizing or extruding the titanium zeolite to form large particle titanium zeolite having a size of 2 microns or greater. If spray dried, pelletized or extruded, the titanium zeolite may additionally comprise a binder or the like and may be molded, spray dried, shaped or extruded into any desired form. Preferred binders include silica, alumina, and titania.

The catalyst of the invention also comprises palladium nanoparticles and support nanoparticles. The palladium nanoparticles of the invention have an average crystallite size less than 100 nm, preferably from 0.1 to 50 nm, and most preferably from 1 to 20 nm. Preferably, the amount of palladium present in the catalyst will be in the range of from 0.01 to 20 weight percent, more preferably from 0.1 to 10 weight percent.

The support nanoparticles are support materials that have an average crystallite size less than 200 nm, preferably from 0.5 to 100 nm, and most preferably from 3 to 60 nm. The support material is preferably an inorganic oxide of Group 2, 3, 4, 5, 6, 13, or 14 elements. Preferred supports include silica, alumina, silica-aluminas, titania, zirconia, niobia, tantalum oxides, molybdenum oxides, tungsten oxides, amorphous titania-silica, amorphous zirconia-silica, amorphous niobia-silica, and the like. Particularly preferred supports include titania, zirconia, niobia, silica, alumina, tantalum oxide, and mixtures thereof. Titania is most preferred.

Preferably, the support nanoparticle has a surface area in the range of about 1 to about 700 $m^2/g$, most preferably from about 10 to about 500 $m^2/g$. Preferably, the pore volume of the support nanoparticle is in the range of about 0.1 to about 4.0 mL/g, more preferably from about 0.5 to about 3.5 mL/g, and most preferably from about 0.8 to about 3.0 mL/g.

The palladium nanoparticles are deposited on the support nanoparticles to form supported palladium nanoparticles. The supported palladium nanoparticles can be produced by any known method. For instance, the palladium and support nanoparticles can be produced together by passing an aerosol comprising a mixture of palladium powder and a support (or a support precursor) through a plasma torch to vaporize the palladium powder and support to produce the supported palladium nanoparticles, which comprise palladium nanoparticles supported on support nanoparticles. See, e.g., U.S. Pat. No. 5,989,648.

The supported palladium nanoparticles are then preferably dispersed in a solvent, and deposited on the titanium zeolite or the carrier to form the catalyst of the invention. Preferably, the supported palladium nanoparticles are transported from the supported palladium nanoparticle formation step by means such as a mechanical pump to the dispersing solvent. Dispersing solvents useful in the present invention include any aqueous or nonaqueous liquid. Suitable dispersing solvents include, but are not limited to, water, oxygenated hydrocarbons such as alcohols, ethers, esters, and ketones, aromatic and aliphatic hydrocarbons such as toluene and hexane, halogenated hydrocarbons such as methylene chloride and chlorobenzene, nitriles such as acetonitrile, and alkylalkanolamines such as 2-dimethylaminoethanol. Aqueous solvents are particularly preferred.

The dispersing solvent may be a pure solvent or a mixture of solvents and may contain additional ingredients, including dispersing aids. Suitable dispersing aids include inorganic and organic soluble materials, such as soluble polymers, surfactants, insoluble particulates, acids, bases, and salts. Surfactants include, but are not limited to, alkylcarboxylic acid salts, alkylsulfonic acid salts, alkylbenzenesulfonic acid salts, alkyl sulfates, alkyl phosphonates, amines, aminoalkylsulfonic acid salts, aminoalkyl phosphates, alkylamine salts, and tertiary ammonium salts of fatty acids or aromatic acids. Preferably, the dispersing aid is a soluble polymer such as poly-N-vinylpyrrolidone, polyvinyl alcohol, polyvinyl acetate, polyacrylic acid, polymethacrylic acid, polyacrylamide, polyvinylimidazole and polyvinylpyrazole poly(vinylpyrrolidone), polyalkylene glycols, poly(propylene oxide), and polydialkylsiloxane. Preferably, the amount of dispersing aid in the solvent can be from 0 to 50%, preferably 0 to 20%, and more preferably 0 to 5%.

The supported palladium nanoparticles are deposited on the titanium zeolite; or the supported palladium nanoparticles are deposited on a carrier having a particle size of 2 microns or greater.

The carrier is any carrier having a particle size of 2 microns or greater, more preferably 5 microns or greater, and most preferably from 5 microns to 100 microns. The carrier is preferably a porous material. Carriers are well-known in the art. For instance, the carrier can be inorganic oxides, clays, carbon, and organic polymer resins. Preferred inorganic oxides include oxides of Group 2, 3, 4, 5, 6, 13, or 14 elements. Particularly preferred inorganic oxide carriers include silica, alumina, silica-aluminas, titania, zirconia, niobium oxides, tantalum oxides, molybdenum oxides, tungsten oxides, amorphous titania-silica, amorphous zirconia-silica, amorphous niobia-silica, and the like. Preferred organic polymer resins include polystyrene, styrene-divinylbenzene copolymers, crosslinked polyethyleneimines, and polybenzimidazole. Suitable carriers also include organic polymer resins grafted onto inorganic oxide carriers, such as polyethylenimine-silica. Preferred carriers also include carbon. Particularly preferred carriers include titania, zirconia, niobia, silica, alumina, silica-alumina, tantalum oxide, titania-silica, zirconia-silica, niobia-silica, and mixtures thereof. Titania is particularly preferred.

The supported palladium nanoparticles may be deposited on the carrier (or titanium zeolite) by any suitable method, including impregnation, adsorption, precipitation, or the like. If deposited on a carrier, the supported palladium nanoparticle-on-carrier material is mixed with titanium zeolite to form the catalyst of the invention.

Preferably, the catalyst of the invention also contains one or more additional metals including lead, bismuth, zinc, copper, tin, or other noble metals such as gold, silver, platinum, iridium, ruthenium, or osmium. Lead, platinum and gold are especially preferred. The typical amount of additional metal present in the catalyst is preferably in the range of from about 0.01 to 10 weight percent, more preferably 0.01 to 2 weight percent. The one or more additional metals may be added into the catalyst during the nanoparticle formation step, e.g., vaporizing an aerosol comprising a mixture of palladium powder, additional metal(s) powder (or an alloy of palladium and one or more additional metals, e.g., a Pd-metal alloy such as Pd—Pb alloy) and support (or support precursor) in a plasma torch. The one or more additional metals may be added into the catalyst by adding one or more additional metal compounds into the supported palladium nanoparticle dispersion, which is then added to the carrier or titanium zeolite as described above. Also, the one or more additional metals may be added to the catalyst by a post-treatment with one or more additional metal compounds or may be added to the carrier or titanium zeolite prior to deposition of the supported palladium nanoparticle. Suitable metal addition methods include impregnation (e.g., by incipient wetness, etc.), adsorption, ion-exchange, deposition-precipitation, or other incorporation methods. Suitable additional metal compounds include nitrates, carboxylates (e.g., acetate), halides (e.g., chlorides, bromides, iodides), cyanides, and sulfides. For example, lead nitrates and carboxylates are particularly preferred.

The catalyst may be encapsulated in a polymer, for example, polystyrenics, polyolefins, polyureas, polyacrylics, polyurethanes, polyesters, polyamides, fluorinated polymers, polysaccharides, polypeptides, polynucleotides, and mixtures thereof. See U.S. Pat. Nos. 6,958,255 and 7,030,255. The catalyst may also be additional comprise a thiol, where the thiol is tethered to the carrier or to the titanium zeolite. See, e.g., U.S. Pat. Nos. 7,453,003 and 7,501,532.

The epoxidation process of the invention comprises contacting an olefin, oxygen, and hydrogen in the presence of the catalyst. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the epoxidation process. Although any sources of oxygen and hydrogen are suitable, molecular oxygen and is molecular hydrogen are preferred.

Epoxidation according to the invention is carried out at a temperature effective to achieve the desired olefin epoxidation, preferably at temperatures in the range of 0-250° C., more preferably, 20-100° C. The molar ratio of hydrogen to oxygen can usually be varied in the range of $H_2:O_2$=1:10 to 5:1 and is especially favorable at 1:5 to 2:1. The molar ratio of oxygen to olefin is usually 2:1 to 1:20, and preferably 1:1 to 1:10. A carrier gas may also be used in the epoxidation process. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are suitable in addition to nitrogen and carbon dioxide. Saturated hydrocarbons with 1-8, especially 1-6, and preferably with 1-4 carbon atoms, e.g., methane, ethane, propane, and n-butane, are also suitable. Nitrogen and saturated $C_1$-$C_4$ hydrocarbons are the preferred inert carrier gases. Mixtures of the listed inert carrier gases can also be used.

Specifically in the epoxidation of propylene, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

Preferably, epoxidation is carried out in the liquid (or supercritical or subcritical) phase. It is advantageous to work at a pressure of 1-100 bars and in the presence of one or more solvents. Suitable solvents include any chemical that is a liquid under reaction conditions, including, but not limited to, oxygenated hydrocarbons such as alcohols, ethers, esters, and ketones, aromatic and aliphatic hydrocarbons such as toluene and hexane, nitriles such as acetonitrile, liquid $CO_2$ (in the supercritical or subcritical state), and water. Preferable solvents include liquid $CO_2$, nitriles, alcohols, ketones, and mixtures thereof, and mixtures of these solvents with water. Preferred nitriles include acetonitrile and other nitriles with appreciable water solubility. Preferred alcohols include lower aliphatic $C_1$-$C_4$ alcohols such as methanol, ethanol, isopropanol, and tert-butanol, or mixtures thereof. Fluorinated alcohols can be used. It is particularly preferable to use mixtures of the cited alcohols with water.

The process may be performed using a continuous flow, semi-batch or batch mode of operation. When a liquid reaction medium is used, the catalyst is preferably in the form of a suspension or fixed-bed.

If epoxidation is carried out in the liquid (or supercritical or subcritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 8. Suitable salts of oxyacids contain an anion and cation. The anion portion of the salt may include anions such as phosphate, monohydrogenphosphate, dihydrogenphosphate, sulfate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Examples include $NH_4$, $NBu_4$, $NMe_4$, Li, Na, K, Cs, Mg, and Ca cations. More preferred buffers include alkali metal phosphate and ammonium phosphate buffers. Buffers may preferably contain a combination of more than one suitable salt. Typically, the concentration of buffer in the solvent is from about 0.0001 M to about 1 M, preferably from about 0.001 M to about 0.3 M. The buffer useful in this invention may also include the addition of ammonia gas to the reaction system.

The following examples merely illustrate the invention. Those skilled in the art will recognize many variations that are within the spirit of the invention and scope of the claims.

EXAMPLE 1

Catalyst Preparation

TS-1 can be made according to any known literature procedure. See, for example, U.S. Pat. No. 4,410,501, DiRenzo, et. al., *Microporous Materials* (1997), Vol. 10, 283, or Edler, et. al., *J. Chem. Soc., Chem. Comm.* (1995), 155. Ti-MWW can be made according to Wu et al., *J. Phys. Chem. B*, 2001, 105, p. 2897. The aqueous dispersions of supported palladium nanoparticles are produced by SDCmaterials, Inc.

Comparative Catalyst 1A (Pd/TiO$_2$): A solution of nitric acid (5 mL, 5 M), deionized water (3 mL), and an aqueous solution of palladium nitrate (0.535 g, 20.64 wt. % Pd) is added by incipient wetness to spray dried titania (10 g, 40 micron size, calcined in air at 700° C.). The solids are calcined in air in a muffle furnace by heating at 10° C./min to 110° C. for 4 hours and then at 2° C./min to 300° C. for 4 hours. These calcined solids are then washed with deionized water (20 mL, three times) and dried in a vacuum oven at 50° C. for 18 hours. The washed solids are calcined in a muffle furnace by heating at 10° C./min to 110° C. for 4 hours and then heating at 2° C./min to 600° C. for 4 hours. The solids are transferred to a quartz tube and reduced with a 4 vol. % hydrogen in nitrogen stream at 100° C. for 1 hour (100 mL/hr), followed by nitrogen for 1 hour while cooling from 100° C. to 23° C. to produce Comparative Catalyst 1A. Comparative Catalyst 1A contains 0.91 wt. % Pd.

Catalyst 1B (nanoPd/nanoTiO$_2$ on TiO$_2$ carrier): An aqueous dispersion (16 mL) containing 3.5 wt. % solids of nano-palladium (6 nm) on nano-TiO$_2$ (20 nm) is added by incipient wetness to spray dried titania (20 g, 40 micron size, calcined in air at 700° C.). The solids are calcined in air by heating at 10° C./min to 110° C. for 4 hours and then at 2° C./min to 300° C. for 4 hours. The calcined solids are transferred to a quartz tube and reduced with a 4 vol. % hydrogen in nitrogen stream at 100° C. for 1 hour (100 mL/hr), followed by nitrogen for 1 hour while cooling from 100° C. to 23° C. to produce Catalyst 1B. Catalyst 1B contains 0.6 wt. % Pd.

Comparative Catalyst 2A (Pd—Pb/TiO$_2$): A solution of 2.56 M nitric acid (2.5 mL), deionized water (5.5 mL), a palladium nitrate solution (0.53 g, 20.64 wt % palladium) and 0.17 wt. % lead nitrate (57.8 wt % Pb) is added by incipient wetness to spray dried titania (10 g, 40 micron size, calcined in air at 700° C.). The solids are calcined, washed, re-calcined, and reduced according to the procedure of Comparative Catalyst 1A to produce Comparative Catalyst 2A. Comparative Catalyst 2A contains 0.9 wt. % Pd and 0.8 wt. % Pb.

Catalyst 2B Pb/nanoPd/nanoTiO$_2$ on TiO$_2$ carrier): Lead nitrate (0.35 g) is dissolved in deionized water (8 mL) and this solution is mixed with an aqueous dispersion (8 mL) containing 7.4 wt. % solids of nano-palladium (6 nm) on nano-TiO$_2$ (20 nm) and the mixture is added by incipient wetness to spray dried titania (20 g, 40 micron size, calcined in air at 700° C.). The solids are calcined and reduced according to the procedure of Example 1B, with the exception that the solids are calcined at 600° C. instead of 300° C. for 4 hours, to produce Catalyst 2B. Catalyst 2B contains 0.5 wt. % Pd and 0.74 wt. % Pb.

Catalyst 2C (nanoPd/nanoPb/nanoTiO$_2$ on TiO$_2$ carrier): Catalyst 2C is prepared according to the procedure of Catalyst 1B except that the dispersion used is prepared by simultaneously vaporizing Pd and Pb powders with TiO$_2$ (metals=4.7 nanometers), and the solids are calcined at 600° C. instead of 300° C. for 4 hours, to produce Catalyst 2C. Catalyst 2C contains 0.9 wt. % Pd and 0.8 wt. % Pb.

Comparative Catalyst 3A (Pd—Pb/TS-1): Lead nitrate (0.07 g) in 16 mL of deionized water is added to 5 mL of 2.56 molar nitric acid to form a lead nitrate solution, and an aqueous solution of palladium nitrate (0.21 g, 20.64 wt. % Pd) is added with mixing. The Pd—Pb solution is then added by incipient wetness to spray dried TS-1 (20 g, 40 micron size, 20% silica binder, calcined in air at 550° C.). The solids are calcined in air by heating at 10° C./min to 110° C. for 4 hours and then at 2° C./min to 300° C. for 4 hours. Then the calcined solids are calcined again and reduced according to the procedure of Example 2B to produce Comparative Catalyst 3A. Comparative Catalyst 3A contains 0.27 wt. % Pd, 0.21 wt. % Pb and 1.8 wt. % Ti.

Catalyst 3B (Pb/nanoPd/nanoTiO$_2$ on TS-1): Lead nitrate (0.132 g) is dissolved in deionized water (38 mL) and this solution is mixed with an aqueous dispersion (2.7 mL) containing 7.4 wt. % solids of nano-palladium (6 nm) on nano-TiO$_2$ (20 nm) and the mixture is added by incipient wetness to spray dried TS-1 (40 g, 40 micron size, 20% silica binder, calcined in air at 550° C.). The solids are calcined, recalcined and reduced according to the procedure of Comparative Catalyst 3A. Catalyst 3B contains 0.18 wt. % Pd, 0.23 wt. % Pb and 1.9 wt % Ti.

Comparative Catalyst 4A (Pd—Pb/Ti-MWW): Lead nitrate (0.025 g) in 13 mL of deionized water (13 mL) is added to 2 mL of 2.56 M nitric acid to form a lead nitrate solution, and an aqueous solution of palladium nitrate (0.08 g, 20.64 wt. % Pd) is added with mixing. The Pd—Pb solution is then added by incipient wetness to spray dried Ti-MWW (8 g, 5 micron size, calcined in air at 530° C.). The solids are calcined, recalcined and reduced according to the procedure of Comparative Catalyst 3A. Comparative Catalyst 4A contains 0.17 wt. % Pd, 0.14 wt. % Pb and 1.2 wt. % Ti.

Catalyst 4B (nanoPd/nanoPb/nanoTiO$_2$ on Ti-MWW): An aqueous dispersion (14.3 mL) containing 0.64 wt. % solids of nano-palladium/nano-lead (7 nm, made by vaporizing a Pd/Pb alloy with TiO$_2$) on nano-TiO$_2$ (20 nm) and the mixture is added by incipient wetness to spray dried Ti-MWW (8 g, 5 micron size, calcined in air at 530° C.). The solids are calcined, recalcined and reduced according to the procedure of Comparative Catalyst 3A. Catalyst 4B contains 0.11 wt. % Pd, 0.14 wt. % Pb and 1.5 wt. % Ti.

EXAMPLE 2

Propylene Epoxidation Reactions

Epoxidation Runs for Catalysts 1A-3B: A 300-cc stainless steel reactor is charged with Catalyst 3A or 3B (0.7 g) or a mixture of TS-1 (0.63 g, 20 g, 40 micron size, 20% silica binder, calcined in air at 550° C.) and one of Catalysts 1A-2C (0.07 g), methanol (100 g) and 13 grams of a buffer (0.1 M aqueous ammonium phosphate, pH=6). The reactor is then charged to 300 psig of a feed consisting of 4% hydrogen, 4% oxygen, 5% propylene, 0.5% methane and the balance nitrogen (volume %). The pressure in the reactor is maintained at 300 psig via a back pressure regulator with the feed gases passed continuously through the reactor at 1600 cc/min (measured at 23°° C. and one atmosphere pressure). In order to maintain a constant solvent level in the reactor during the run, the oxygen, nitrogen and propylene feeds are passed through a two-liter stainless steel vessel (saturator) preceding the reactor containing 1.5 liters of methanol. The reactor is stirred at 1500 rpm. The reaction mixture is heated to 60° C. and the gaseous effluent is analyzed by an online GC every hour and the liquid analyzed by offline GC at the end of the 18 hour run. Propylene oxide and equivalents ("POE"), which include propylene oxide ("PO"), propylene glycol ("PG"), and propylene glycol methyl ethers ("PM"s), are produced during the reaction, in addition to propane formed by the hydrogenation of propylene.

Epoxidation Runs for Catalysts 4A and 4B: A 300 cc stainless steel reactor is charged with Catalyst 4A or 4B (0.7 g), tert-butanol (86 g), deionized water (25 g), and 13 grams of a buffer (0.1 M aqueous ammonium phosphate, pH=6). The epoxidation is then run according to the procedure for epoxidation runs using catalysts 1A-3B. Propylene oxide and equivalents ("POE"), which include propylene oxide ("PO"), propylene glycol ("PG"), and propylene glycol tert-butyl ethers, are produced during the reaction, in addition to propane formed by the hydrogenation of propylene.

The epoxidation results (see Table 1) show that supported palladium nanoparticles on titanium zeolite (TS-1 or Ti-MWW) catalysts are more active and more selective than comparable catalysts produced by depositing palladium compounds directly onto the titanium zeolite. The results also show that catalyst mixtures comprising titanium zeolite and supported palladium nanoparticles show increased catalyst activity compared to comparable catalysts produced by depositing palladium compounds onto the carrier.

TABLE 1

Epoxidation Results

| Catalyst | Catalyst Productivity[1] | Propylene Selectivity (%)[2] |
|---|---|---|
| TS-1 + 1A* | 0.62 | 75 |
| TS-1 + 1B | 0.86 | 68 |
| TS-1 + 2A* | 0.55 | 95 |
| TS-1 + 2B | 0.59 | 97 |
| TS-1 + 2C | 0.8 | 95 |
| 3A* | 0.44 | 69 |
| 3B | 0.72 | 95 |

TABLE 1-continued

Epoxidation Results

| Catalyst | Catalyst Productivity[1] | Propylene Selectivity (%)[2] |
|---|---|---|
| 4A* | 0.36 | 95 |
| 4B | 0.58 | 97 |

[1]Productivity = grams POE produced/gram of catalyst per hour.
[2]Propylene Selectivity = 100 − (moles propane/moles POE + moles propane) × 100.
*Comparative Example

We claim:

1. A process for producing an epoxide comprising reacting an olefin, hydrogen and oxygen in the presence of a catalyst comprising palladium nanoparticles, support nanoparticles having an average crystallite size of less than 200 nm, and a titanium zeolite having a particle size of 2 microns or greater, wherein the palladium nanoparticles are deposited on the support nanoparticles to form supported palladium nanoparticles, and:
    (a) the supported palladium nanoparticles are deposited on the titanium zeolite; or
    (b) the supported palladium nanoparticles are deposited on a carrier having a particle size of 2 microns or greater.

2. The process of claim 1 wherein the titanium zeolite is a titanium silicalite.

3. The process of claim 1 wherein the support nanoparticles are selected from the group consisting of titania, zirconia, niobia, silica, alumina, tantalum oxide, and mixtures thereof.

4. The process of claim 1 wherein the carrier is selected from the group consisting of titania, zirconia, niobia, silica, alumina, silica-alumina, tantalum oxide, titania-silica, zirconia-silica, niobia-silica, and mixtures thereof.

5. The process of claim 4 wherein the carrier is titania.

6. The process of claim 4 wherein the carrier has a particle size of 5 microns or greater.

7. The process of claim 1 wherein the olefin is a $C_2$-$C_6$ olefin.

8. The process of claim 1 wherein the catalyst further comprises lead.

9. A catalyst comprising palladium nanoparticles, support nanoparticles having an average crystallite size of less than 200 nm, and a titanium zeolite having a particle size of 2 microns or greater, wherein the palladium nanoparticles are deposited on the support nanoparticles to form supported palladium nanoparticles, and:
    (a) the supported palladium nanoparticles are deposited on the titanium zeolite; or
    (b) the supported palladium nanoparticles are deposited on a carrier having a particle size of 2 microns or greater.

10. The catalyst of claim 9 wherein the support nanoparticles are selected from the group consisting of titania, zirconia, niobia, silica, alumina, tantalum oxide, and mixtures thereof.

11. The catalyst of claim 9 wherein the titanium zeolite is TS-1 or Ti-MWW.

12. The catalyst of claim 9 wherein the carrier is selected from the group consisting of titania, zirconia, niobia, silica, alumina, silica-alumina, tantalum oxide, titania-silica, zirconia-silica, niobia-silica, and mixtures thereof.

13. The catalyst of claim 9 wherein the carrier is titania.

14. The catalyst of claim 9 wherein the carrier has a particle size of 5 microns or greater.

15. The catalyst of claim 9 wherein the catalyst further comprises lead, gold, or platinum.

16. The process of claim 1 wherein the average crystallite size of the support nanoparticles is from 0.5 to 100 nm.

17. The process of claim 1 wherein the average crystallite size of the support nanoparticles is from 3 to 60 nm.

18. The catalyst of claim 9 wherein the average crystallite size of the support nanoparticles is from 0.5 to 100 nm.

19. The catalyst of claim 9 wherein the average crystallite size of the support nanoparticles is from 3 to 60 nm.

* * * * *